(12) United States Patent
Tipping et al.

(10) Patent No.: US 9,918,750 B2
(45) Date of Patent: Mar. 20, 2018

(54) METHOD, SYSTEM, AND APPARATUS FOR TEMPORARY ANTERIOR CERVICAL PLATE FIXATION

(71) Applicant: Osseus Fusion Systems, LLC, Dallas, TX (US)

(72) Inventors: Chase D. Tipping, Dallas, TX (US); Glenn Lieberman, Laconia, NH (US); Anthony Salerni, Laconia, NH (US)

(*) Notice: Subject to any disclaimer, the term of this patent is extended or adjusted under 35 U.S.C. 154(b) by 0 days.

(21) Appl. No.: 15/254,686

(22) Filed: Sep. 1, 2016

(65) Prior Publication Data
US 2018/0036042 A1  Feb. 8, 2018

Related U.S. Application Data

(60) Provisional application No. 62/371,166, filed on Aug. 4, 2016.

(51) Int. Cl.
| A61B 17/70 | (2006.01) |
| A61B 17/80 | (2006.01) |
| A61B 17/74 | (2006.01) |
| A61B 17/86 | (2006.01) |
| A61B 17/88 | (2006.01) |
| A61B 17/84 | (2006.01) |

(52) U.S. Cl.
CPC ........ *A61B 17/7059* (2013.01); *A61B 17/74* (2013.01); *A61B 17/808* (2013.01); *A61B 17/8057* (2013.01); *A61B 17/846* (2013.01); *A61B 17/8635* (2013.01); *A61B 17/8897* (2013.01)

(58) Field of Classification Search
CPC .................................................. A61B 17/7059
See application file for complete search history.

(56) References Cited

U.S. PATENT DOCUMENTS

| 5,951,557 | A | 9/1999 | Luter | |
| 6,152,927 | A * | 11/2000 | Farris | A61B 17/7059 606/287 |
| 6,652,525 | B1 * | 11/2003 | Assaker | A61B 17/7059 606/296 |
| 6,740,088 | B1 * | 5/2004 | Kozak | A61B 17/7055 606/280 |
| 9,277,943 | B2 | 3/2016 | Holly et al. | |
| 9,339,311 | B1 * | 5/2016 | Tsai | A61B 17/74 |
| 9,775,652 | B2 * | 10/2017 | Altarac | A61B 17/7058 |
| 2001/0014807 | A1 * | 8/2001 | Wagner | A61B 17/7059 606/279 |
| 2002/0120273 | A1 * | 8/2002 | Needham | A61B 17/1728 606/281 |
| 2003/0060828 | A1 * | 3/2003 | Michelson | A61B 17/7059 606/71 |
| 2004/0034352 | A1 * | 2/2004 | Needham | A61B 17/8042 606/86 R |
| 2004/0176776 | A1 * | 9/2004 | Zubok | A61B 17/7059 606/96 |

(Continued)

*Primary Examiner* — Ellen C Hammond
*Assistant Examiner* — Stuart S Bray
(74) *Attorney, Agent, or Firm* — Merle W. Richman III

(57) ABSTRACT

Embodiments of bony region stabilization systems, apparatus, and methods are described generally herein including implanting a bony segment fixation system 10 with retention modules 20 including a fenestration 22 sized for temporary constructs 122, 132. Other embodiments may be described and claimed.

20 Claims, 17 Drawing Sheets

(56) References Cited

U.S. PATENT DOCUMENTS

| | | | |
|---|---|---|---|
| 2004/0193272 A1* | 9/2004 | Zubok | A61B 17/8042 623/17.11 |
| 2004/0210217 A1* | 10/2004 | Baynham | A61B 17/686 606/295 |
| 2004/0220566 A1* | 11/2004 | Bray | A61B 17/7059 606/252 |
| 2005/0010226 A1* | 1/2005 | Grady, Jr. | A61B 17/746 606/281 |
| 2005/0192577 A1* | 9/2005 | Mosca | A61B 17/1615 606/86 B |
| 2005/0283152 A1* | 12/2005 | Lindemann | A61B 17/7059 606/281 |
| 2006/0122603 A1* | 6/2006 | Kolb | A61B 17/7059 606/287 |
| 2006/0293669 A1* | 12/2006 | Lindemann | A61B 17/7059 606/86 A |
| 2007/0083203 A1* | 4/2007 | Ribeiro | A61B 17/1604 606/279 |
| 2007/0123884 A1* | 5/2007 | Abdou | A61B 17/8042 606/279 |
| 2007/0162013 A1* | 7/2007 | Jacene | A61B 17/1728 606/288 |
| 2008/0097443 A1* | 4/2008 | Campbell | A61B 17/7059 606/281 |
| 2008/0300634 A1* | 12/2008 | Gray | A61B 17/7059 606/280 |
| 2009/0036933 A1* | 2/2009 | Dube | A61B 17/1655 606/282 |
| 2009/0062863 A1* | 3/2009 | Peppers | A61B 17/8038 606/289 |
| 2009/0105831 A1* | 4/2009 | Jones | A61B 17/7059 623/17.16 |
| 2009/0149888 A1* | 6/2009 | Abdelgany | A61B 17/7059 606/286 |
| 2009/0171396 A1* | 7/2009 | Baynham | A61B 17/686 606/280 |
| 2009/0192549 A1* | 7/2009 | Sanders | A61B 17/7059 606/280 |
| 2009/0270927 A1* | 10/2009 | Perrow | A61B 17/7059 606/286 |
| 2009/0287257 A1* | 11/2009 | Hagen | A61B 17/7059 606/289 |
| 2009/0312758 A1* | 12/2009 | Petit | A61B 17/74 606/60 |
| 2010/0262193 A1 | 10/2010 | Frigg et al. | |
| 2011/0022097 A1* | 1/2011 | Walker | A61B 17/8033 606/296 |
| 2011/0029023 A1* | 2/2011 | Tornier | A61B 17/8042 606/289 |
| 2011/0106159 A1* | 5/2011 | Nazeck | A61B 17/7059 606/246 |
| 2011/0118784 A1* | 5/2011 | Baynham | A61B 17/7059 606/264 |
| 2011/0184415 A1* | 7/2011 | Anderson | A61B 17/7059 606/70 |
| 2011/0319943 A1* | 12/2011 | Donahoe | A61B 17/7059 606/290 |
| 2012/0022593 A1* | 1/2012 | Kovach | A61B 17/7059 606/264 |
| 2012/0065690 A1* | 3/2012 | Perrow | A61B 17/7059 606/294 |
| 2012/0179207 A1* | 7/2012 | Mekhail | A61B 17/7059 606/281 |
| 2012/0226319 A1* | 9/2012 | Armstrong | A61B 17/7059 606/279 |
| 2012/0245641 A1* | 9/2012 | Mekhail | A61B 17/7059 606/279 |
| 2013/0030465 A1* | 1/2013 | Hess | A61B 17/7059 606/246 |
| 2013/0053887 A1* | 2/2013 | Predick | A61B 17/7059 606/246 |
| 2013/0053895 A1* | 2/2013 | Stoll | A61B 17/8028 606/279 |
| 2013/0317502 A1* | 11/2013 | Overes | A61B 17/74 606/66 |
| 2014/0243905 A1* | 8/2014 | Cavallazzi | A61B 17/746 606/286 |
| 2015/0080969 A1* | 3/2015 | Holly | A61B 17/7059 606/286 |
| 2015/0094774 A1* | 4/2015 | Swann | A61B 17/8042 606/291 |
| 2015/0100094 A1* | 4/2015 | Milz | A61B 17/7059 606/280 |
| 2015/0230831 A1* | 8/2015 | Altarac | A61B 17/7059 606/246 |
| 2015/0245859 A1* | 9/2015 | McMillen | A61B 17/7059 606/289 |
| 2015/0320452 A1* | 11/2015 | Binder | A61B 17/1728 606/70 |
| 2016/0066968 A1* | 3/2016 | Orsak | A61B 17/746 606/71 |
| 2016/0128737 A1* | 5/2016 | Coric | A61B 17/7059 606/279 |
| 2016/0128746 A1* | 5/2016 | Dunaway | A61B 17/8042 606/246 |
| 2016/0166393 A1* | 6/2016 | Visser | A61B 17/68 623/19.14 |
| 2016/0206351 A1* | 7/2016 | Eom | A61B 17/80 |
| 2016/0310289 A1* | 10/2016 | Arlet | A61F 2/447 |
| 2016/0324554 A1* | 11/2016 | Suh | A61B 17/56 |
| 2017/0007300 A1* | 1/2017 | Garrido | A61B 17/7059 |
| 2017/0189077 A1* | 7/2017 | Blain | A61B 17/7059 |
| 2017/0209186 A1* | 7/2017 | Aferzon | A61B 17/7058 |
| 2017/0215930 A1* | 8/2017 | Lauf | A61B 17/7059 |
| 2017/0224388 A1* | 8/2017 | Walker | A61B 17/7059 |
| 2017/0238974 A1* | 8/2017 | Konieczynski | A61B 17/7059 |

* cited by examiner

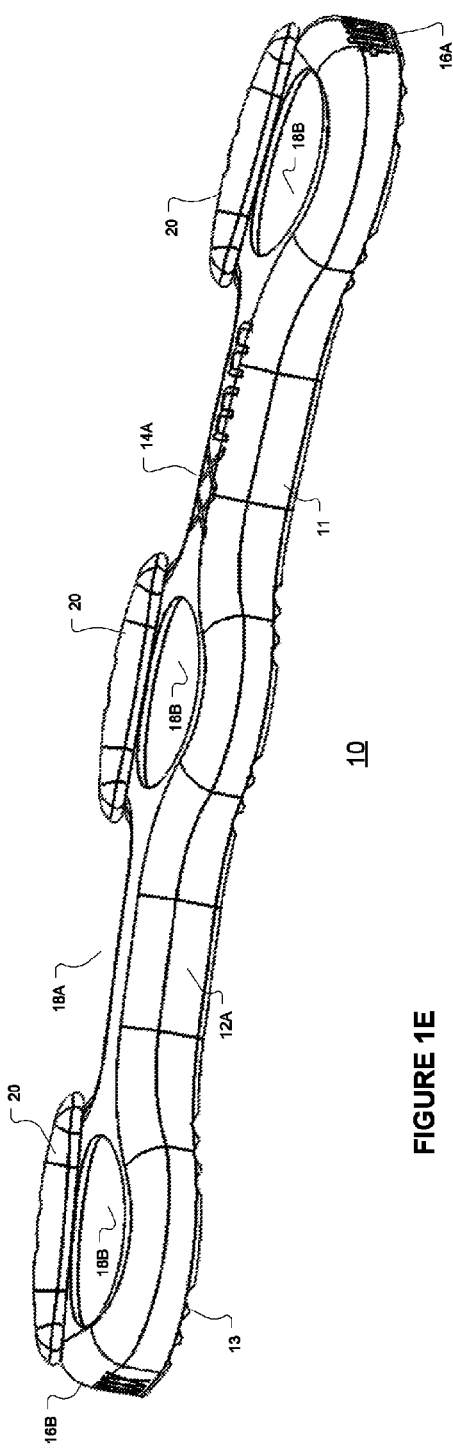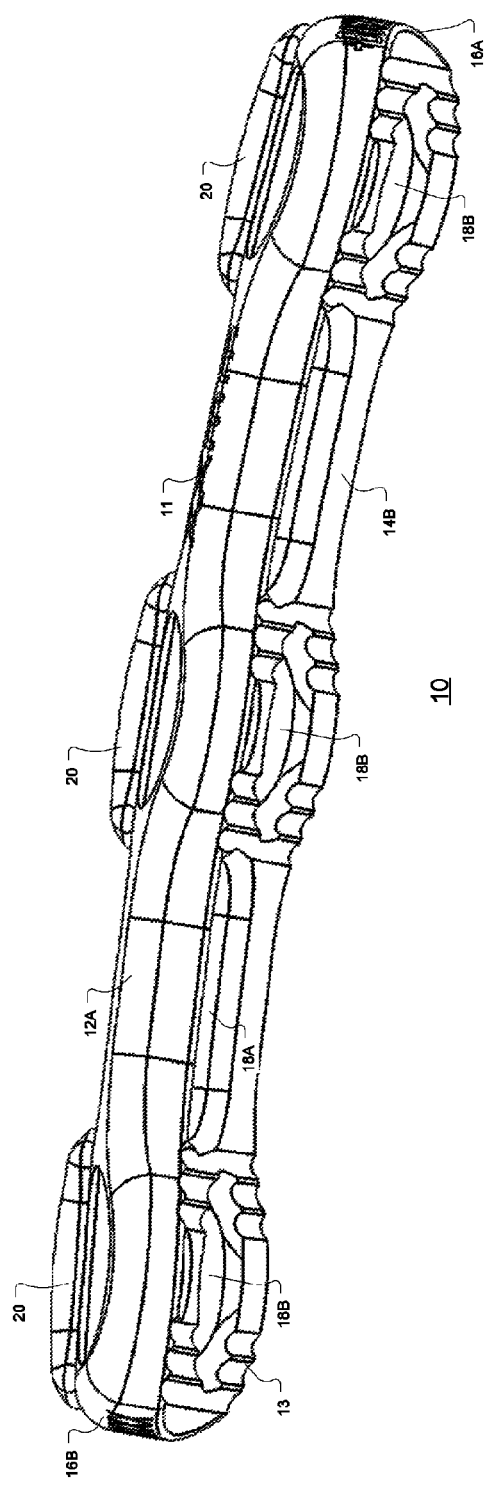
FIGURE 1E
FIGURE 1F

10

10

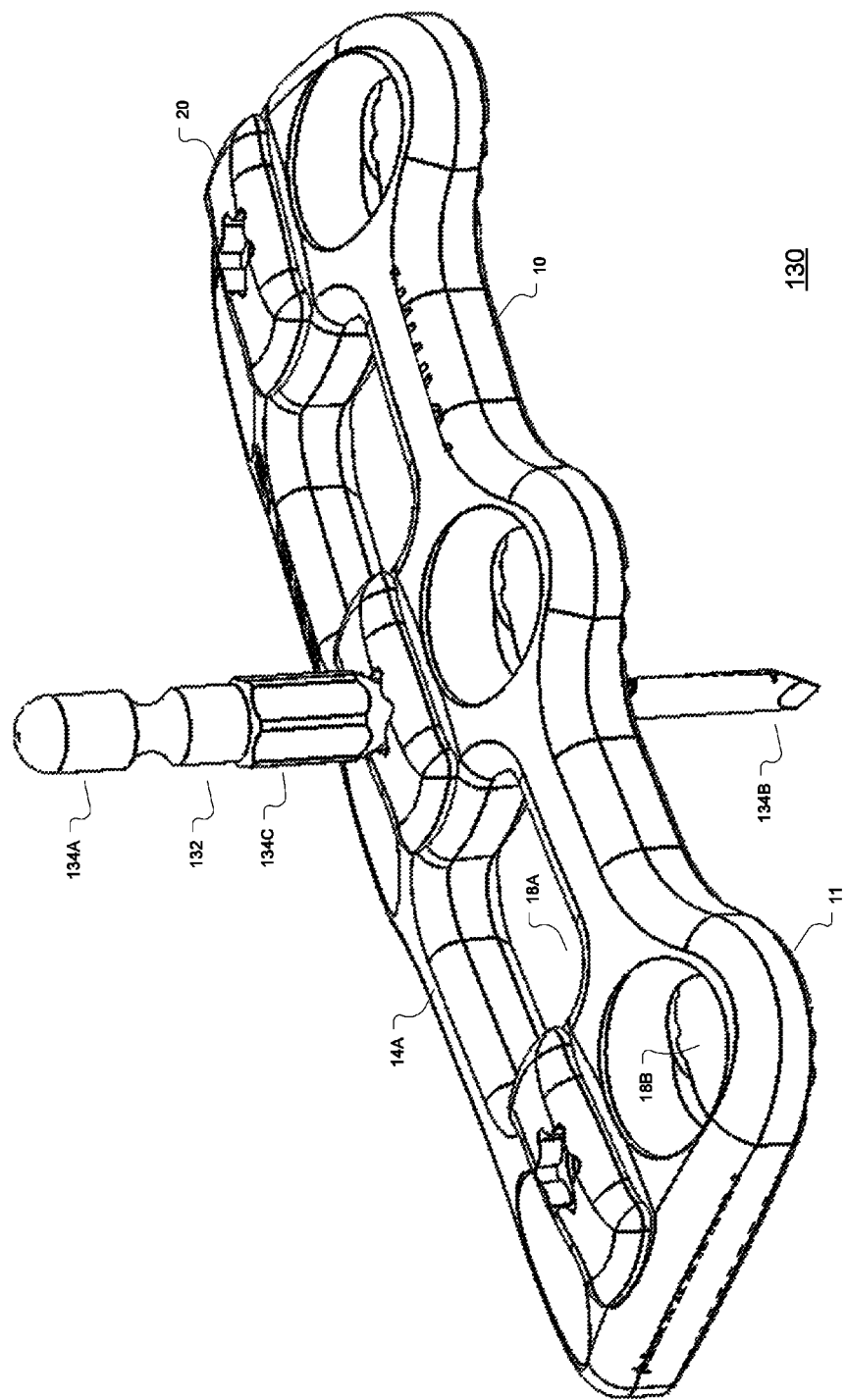

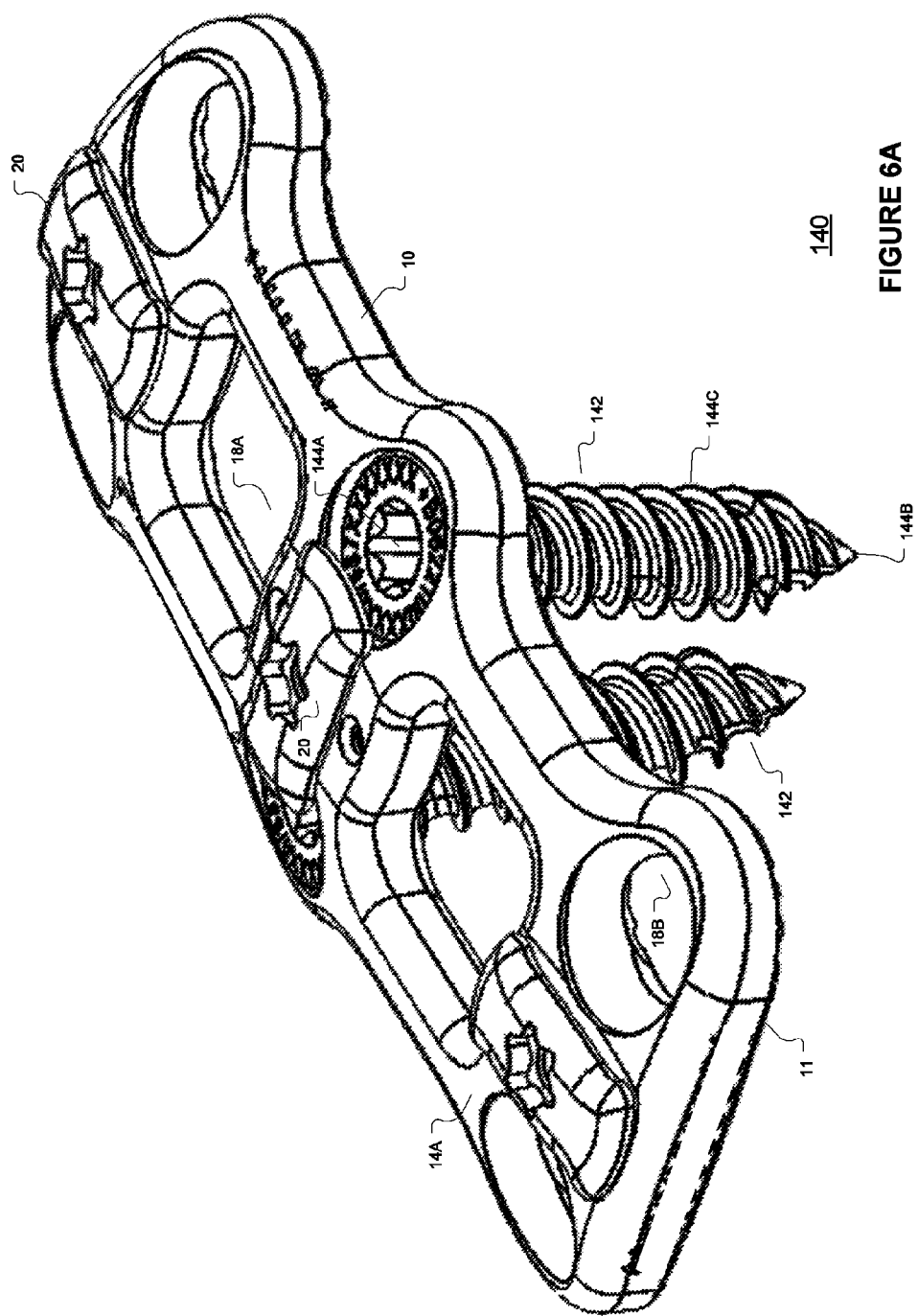

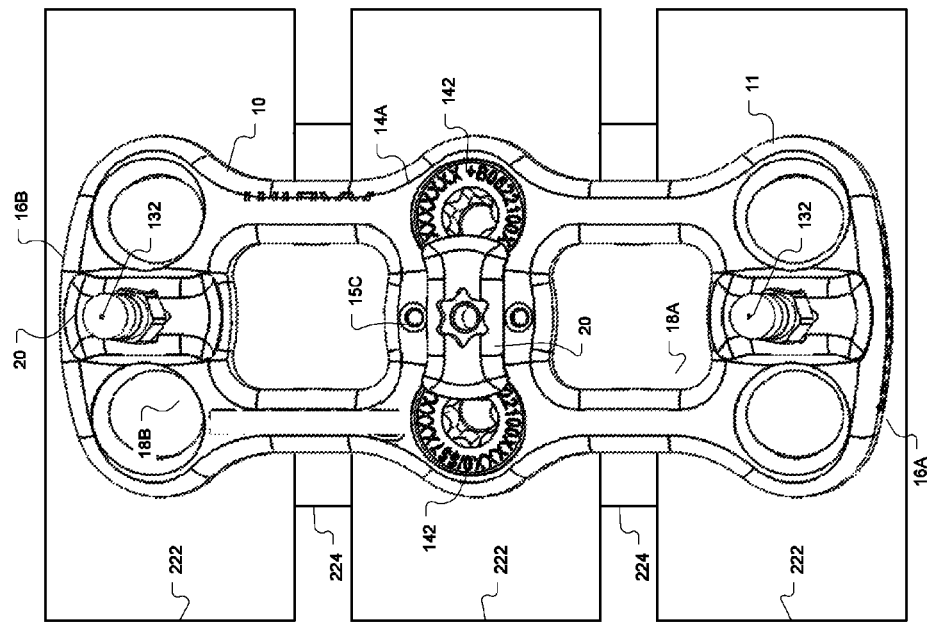
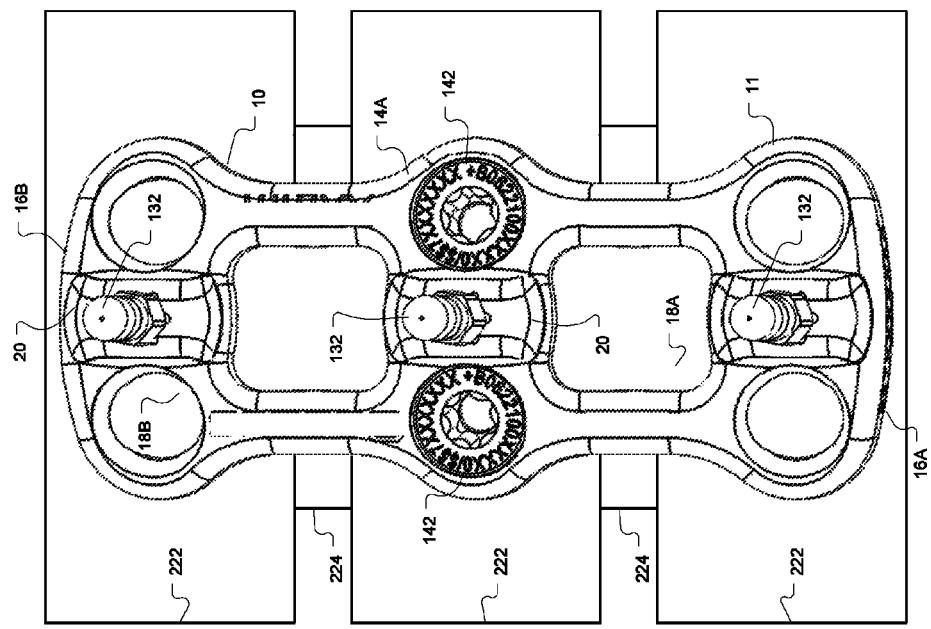

US 9,918,750 B2

METHOD, SYSTEM, AND APPARATUS FOR TEMPORARY ANTERIOR CERVICAL PLATE FIXATION

TECHNICAL FIELD

Various embodiments described herein relate generally to stabilizing mammalian bony segments, including systems and methods to employ an elongated element to stabilize or couple one or more mammalian bony segments.

BACKGROUND INFORMATION

It may be desirable to stabilize or couple one or more bony segments via an elongated element, the present invention provides methods, systems, and instruments for such treatment and deploying such treatment.

BRIEF DESCRIPTION OF THE DRAWINGS

FIG. 1E is a simplified left side view of a bony segment fixation system according to various embodiments.

FIG. 1F is a simplified left side, partial back side view of a bony segment fixation system according to various embodiments.

FIG. 4A is a simplified, isometric view of a bony segment fixation system operatively coupled with a fixation pin via a retention module according to various embodiments.

FIG. 6A is a simplified, isometric view of a bony segment fixation system operatively coupled with several bony segment fixation elements according to various embodiments.

FIG. 8E is a simplified, front view of a bony segment fixation system operatively coupled to a first, center bony segment via a third fixation pin in its center retention module, a first bony fixation element in a left, center bony fixation element fenestration, and a second bony fixation element in a right, center bony fixation element fenestration, operatively coupled to a second, upper bony segment via a first fixation pin in its upper retention module, and operatively coupled to a third, lower bony segment via a second fixation pin in its lower retention module according to various embodiments.

FIG. 8F is a simplified, front view of a bony segment fixation system operatively coupled to a first, center bony segment a first bony fixation element in a left, center bony fixation element fenestration and a second bony fixation element in a right, center bony fixation element fenestration, the center retention module rotated into a back-out prevention mode, operatively coupled to a second, upper bony segment via a first fixation pin in its upper retention module, and operatively coupled to a third, lower bony segment via a second fixation pin in its lower retention module according to various embodiments.

DETAILED DESCRIPTION

Figure 1A:
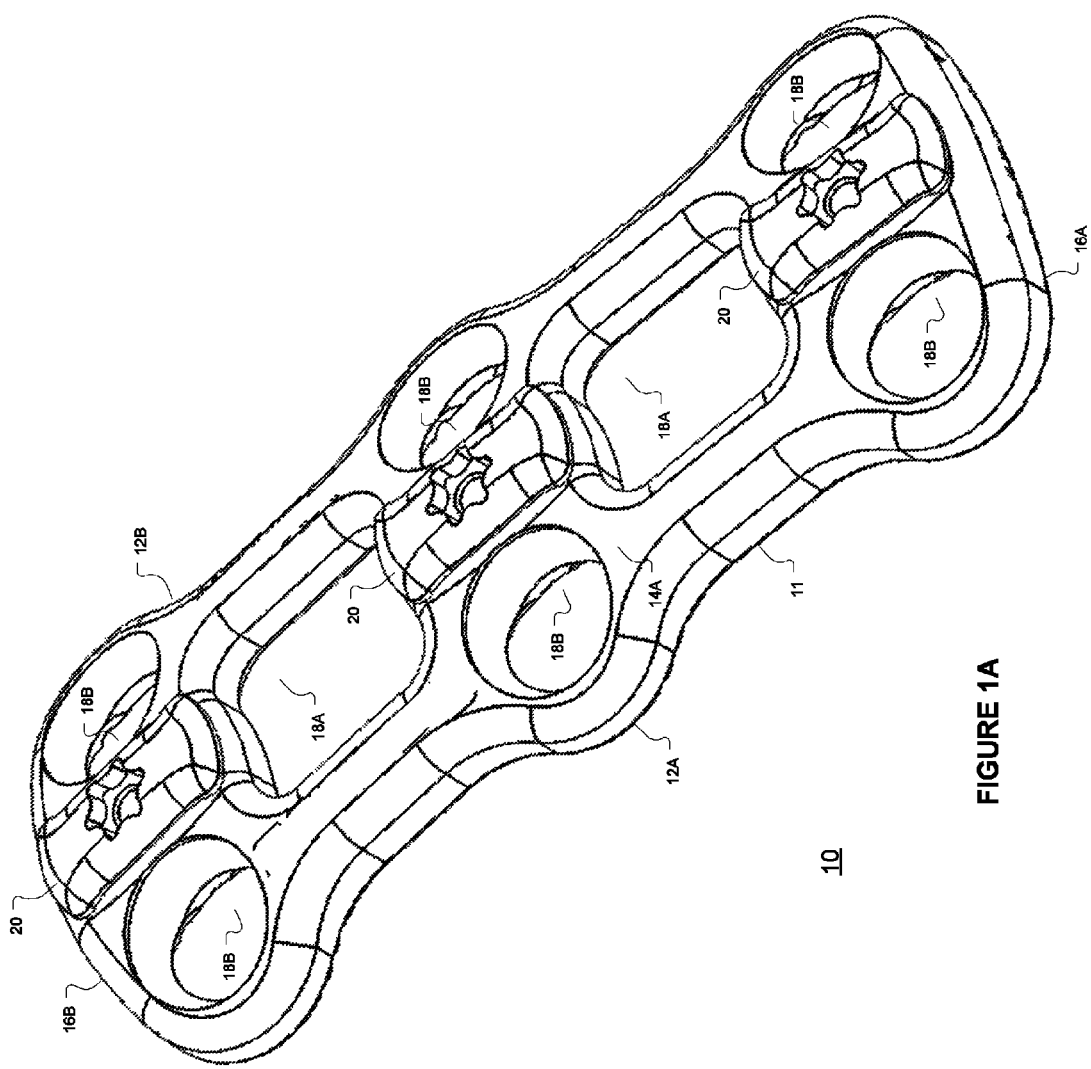
FIG. 1A is a simplified, isometric front side view of a bony segment fixation system according to various embodiments.

It may be desirable to couple one or more bony regions or segments 222 to enable the regions to become stabilized, joined, or fused together. The bony segments 222 may be separated by one or more non-bony elements 224, for example the bony segments 222 may be vertebra separated by spinal discs 224 in a cervical, thoracic, or lumbar region of a mammal including a human. In another embodiment the bony segments 222 may be part of a single, fractured bone to be stabilized such a femur or other long mammalian bone.

A bony segment fixation system 10 that is sized to span one or more bony segments 222 to be stabilized, joined, or fused together may be employed along with bony fixation elements 142 to effectively stabilize, join, or fuse together two or more of the bony segments 222. The bony fixation elements 142 may include bone screws, pins, or other bony region coupling or fixation elements. As part of the process of implanting such a bony segment fixation system 10 and bony fixation elements 142, a practitioner (such as a surgeon) may employ temporary constructs to ensure the bony segment fixation system 10 is ideally placed relative to bony segments 222 to be effected prior to placement of the bony segment fixation system 10 and implantation of one or more bony fixation elements 142.

The temporary constructs may include guide wires 122 and fixation pins 132. The bony segment fixation system 10 may also desirably include one or more retention modules 20 that are configurable to limit or prevent bony fixation elements 142 dislocation from bony segments 222 and limit or prevent projection of bony fixation elements 142 beyond a front surface 14A of the bony segment fixation system 10. The use of the temporary constructs 122, 132 and retention modules 20 may add complexity to such a fixation architecture 100 including the bony segment fixation system 10 and to the procedure(s) required to implant such fixation architecture 100. Fixation architecture 100 according to an embodiment of the invention provides less complex components 10, 20, 122, 132, 142, and procedure(s) 150 for implanting components 10, 20, 122, 132, 142 of fixation architecture 100.

Figure 1B:
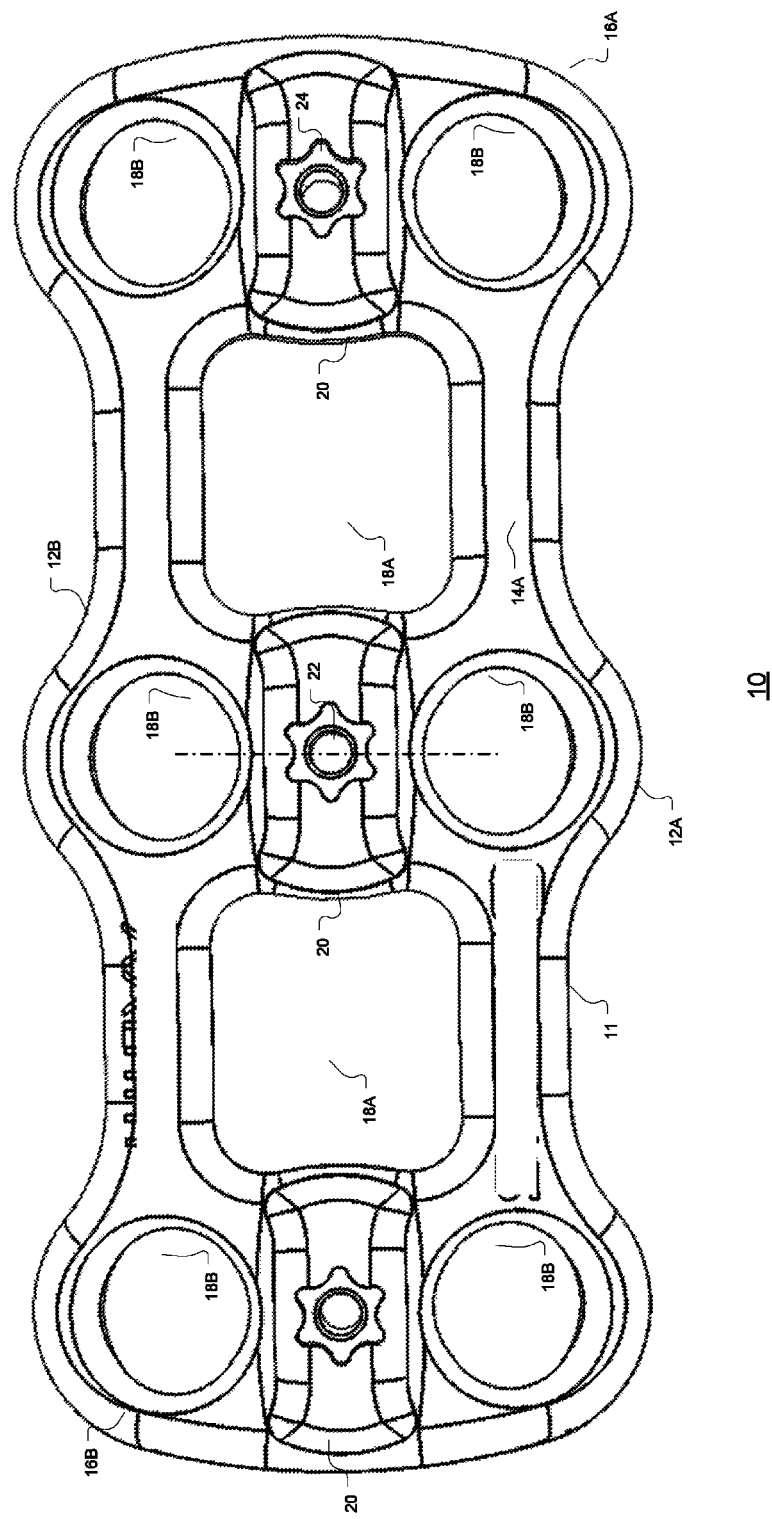
FIG. 1B is a simplified front side view of a bony segment fixation system according to various embodiments.
Figure 1C:
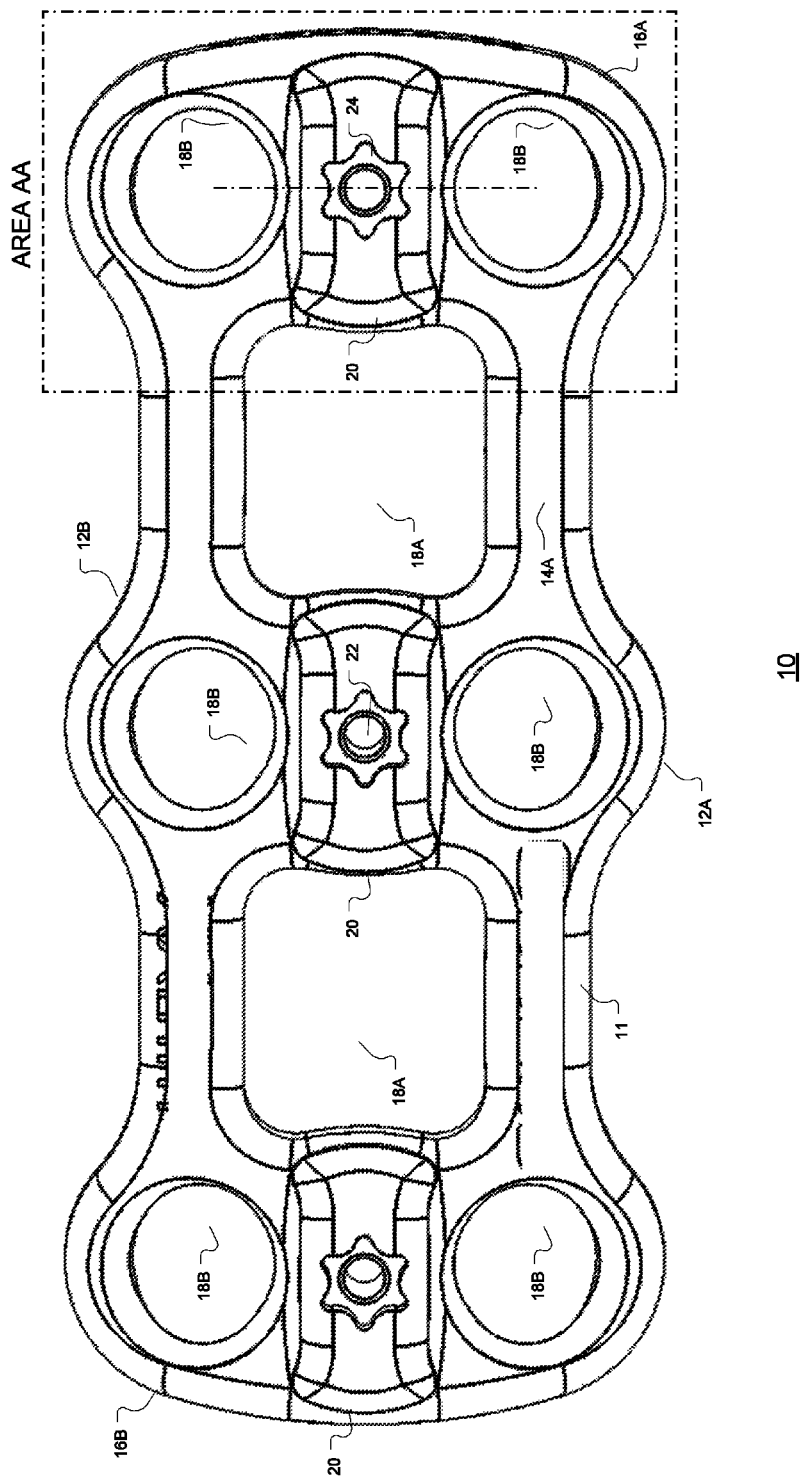
FIG. 1C is a simplified tilted front side view of a bony segment fixation system according to various embodiments.
Figure 1D:
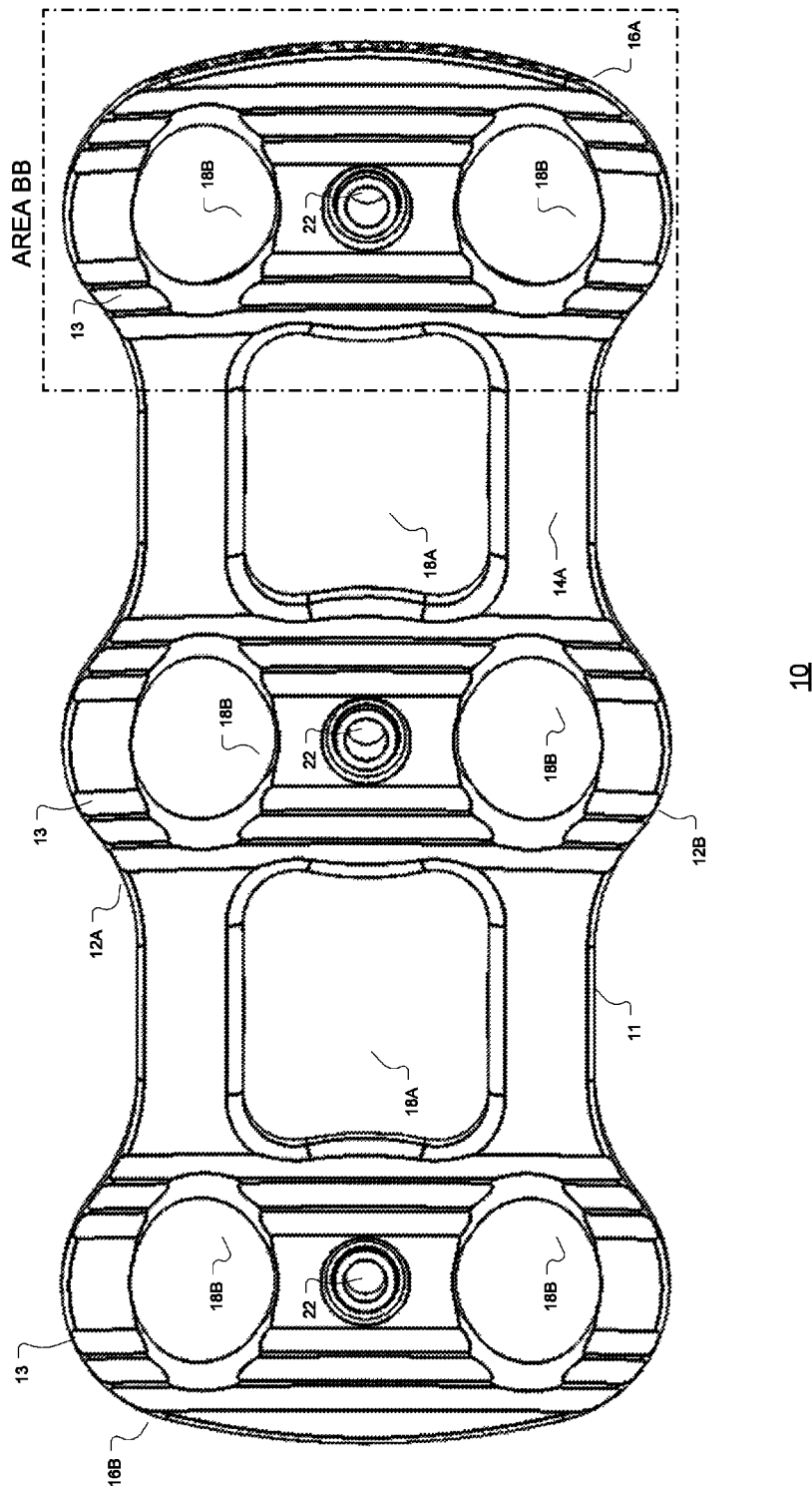
FIG. 1D is a simplified back side view of a bony segment fixation system according to various embodiments.

FIG. 1A is a simplified, isometric front side view, FIG. 1B is a simplified front side view, FIG. 1C is a simplified tilted front side view, FIG. 1D is a simplified back side view, FIG. 1E is a simplified left side view, and FIG. 1F is a simplified left side, partial back side view of a bony segment fixation system 10 according to various embodiments. As shown in FIGS. 1A-1F, the bony segment fixation system 10 may include an elongated plate or planar fixation element 11 including several fenestrations 18A, 18B, and further include several bony fixation elements 142 retention modules 20.

The planar fixation element 11 may have a length extending from its bottom edge 16A to the its top edge 16B. The fixation element's 11 length may vary based on the intended application. In an embodiment, the planar fixation element 11 may be sized to span two or more cervical vertebra of a mammal and may have a length from about 15 mm to 40 mm when intended to span two vertebrae in an embodiment. The fixation element may have a length from about 35 mm to 60 mm when intended to span three vertebrae. The fixation element may have a length from about 50 mm to 80 mm when intended to span four vertebrae and may have a length from about 65 mm to 110 mm when intended to span five vertebrae.

The planar fixation element 11 may have a width extending from its left side 12A to the its right side 12B. The fixation element's 11 width may vary along its length as shown in FIG. 1A where its width may be greater about various fenestrations 18B where fenestrations 18B are sized to accommodate bony fixation elements 142. The fixation element's 11 width may vary from about 10 mm to 40 mm based on the intended application in an embodiment. The planar fixation element 11 may also have a thickness extending from its back side 14B to its top side 14A. The fixation element's 11 thickness may vary along its length and width and be about 2 mm to 7 mm as function of the fixation system's 10 intended application in an embodiment.

In an embodiment, the planar fixation element 11 may be curved along its length as shown in FIG. 1E. The fixation element's 11 curvature along its length may vary as a function of its intended application. In an embodiment, the fixation element's 11 curvature along its length may be about 1 to 7 degrees. The fixation element's 11 curvature along its length may be selected to support natural lordosis of the bony segments 222 (vertebra in an embodiment) to be stabilized. Further in an embodiment, the planar fixation element 11 may be curved along its width as shown in FIG. 1F. The fixation element's 11 curvature along its width may also vary as a function of its intended application. In an embodiment, the fixation element's 11 curvature along its width may be about 1 to 7 degrees. The fixation element's 11 curvature along its width may be selected based on the natural curvature of the bony segments 222 to be stabilized.

Figure 7:
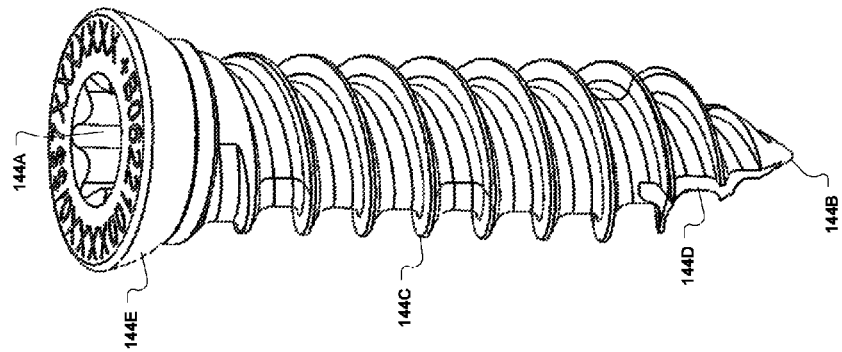
FIG. 7 is a simplified, side view of a bony segment fixation element according to various embodiments.

As also shown in FIG. 1F, the planar fixation element 11 may include several curved serrations 13 along its length and extending across its width on its bottom side 14B. The serrations 13 may provide additional surface area and engagement of bony segments 222 to be stabilized by the bony segment fixation system 10. In an embodiment, a bony fixation element 142 may include a bone screw. FIG. 7 is a simplified, side view of a bony segment fixation element, in particular a bone screw 142 according to various embodiments. As shown in FIG. 7, the bony fixation element 142 may include a head 144E, a tool interface 144A, a threaded shaft 144C, a self-tapping section 144D, and a distal end 144B.

The threaded shaft 144C may have a maximum diameter. In an embodiment, the fixation element's 142 threaded shaft 144C maximum diameter may vary as a function of intended application and be about 2.0 mm to 8.0 mm. The fixation element's 142 head 144E may have a maximum diameter greater than fixation element's 142 threaded shaft 144C maximum diameter. The fixation element's 142 head 144E may have a partially spherical shape along its sides. The fixation element's 142 head 144E top surface may be substantially flat or slightly convex in an embodiment. The fixation element's 142 tool interface 144A may be inset or female to receive a corresponding male tool interface.

As shown in FIGS. 1A-1F, the planar fixation element 11 may include a plurality of bony fixation element fenestrations 18B. The fenestrations 18B form circular or semicircular openings between the fixation element's front side 14A and back side 14B. The bony fixation element fenestrations' 18B minimum diameter may be greater than the bony fixation element's 142 shaft's 144C maximum diameter but less than the bony fixation element's 142 head's 144E maximum diameter. The fenestrations 18B walls formed between the front side 14A and back side 14B may be concave or partially spherical in relief, enabling a bony fixation element's 142 head 144E to pivot when positioned therein. The planar fixation element 11 may include a bony fixation element fenestration 18B for each bony segment 222 to be stabilized or two or more fenestrations 18B for each bony segment 222 as shown in FIG. 8E. As shown in FIGS. 1A-1F, a planar fixation element or plate 11 may also include a large, centered fenestration 18A between levels or fenestrations 18B. The large, centered fenestration 18A may enable a practitioner to visualize regions of bony segments 222, areas 224 between bony segments 222. The large fenestration may also lower the weight of the planar fixation element 11 and enable an implant to be inserted there-through.

Figure 2B:
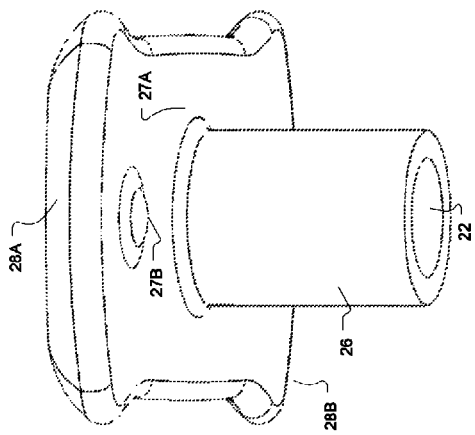
FIG. 2B is a simplified, isometric back side view of a bony fixation element retention module according to various embodiments.
Figure 2D:
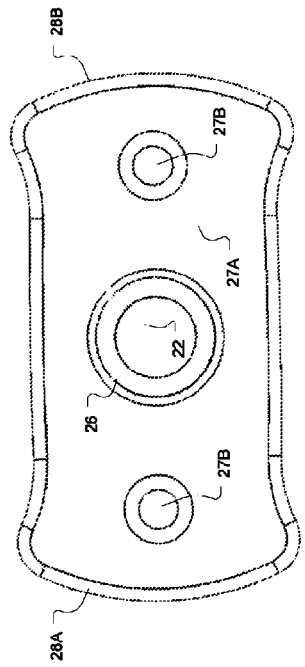
FIG. 2D is a simplified, back view of a bony fixation element retention module according to various embodiments.
Figure 2A:
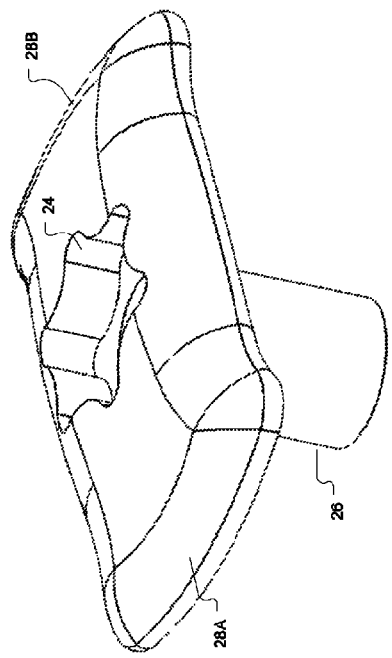
FIG. 2A is a simplified, isometric front side view of a bony fixation element retention module according to various embodiments.
Figure 2C:
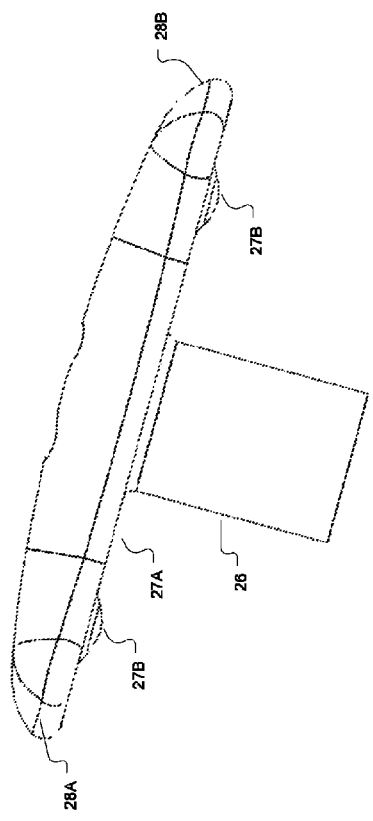
FIG. 2C is a simplified, left side view of a bony fixation element retention module according to various embodiments.

As described it may be desirable to prevent bony fixation elements 142 from protruding, dislodging, or backing-out of a bony fixation element fenestration 18B once implanted into a bony segment. The bony segment fixation system 10 may include a plurality of retention modules 20. In an embodiment, the bony segment fixation system 10 may include a retention module 20 for each bony segment 222 to be stabilized. FIG. 2A is a simplified, isometric front side view, FIG. 2B is a simplified, isometric back side view, FIG. 2C is a simplified, left side view, and FIG. 2D is a simplified, back view of a bony fixation element 142 retention module 20 according to various embodiments.

Figure 1G:
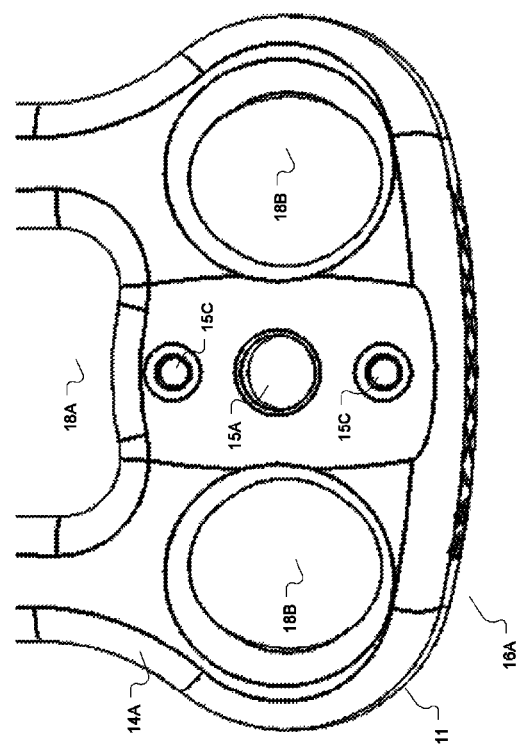
FIG. 1G is a simplified front side view of area AA of the bony segment fixation system shown in FIG. 1C with a retention module removed according to various embodiments.

As shown in FIGS. 2A-2D, the retention module 20 may include a tool interface 24, a cylindrical extension 26 with a fenestration 22 extending there-through, a lower side 27A, a left arm 28A, and a right arm 28B. In an embodiment the lower side may include a detent or protrusion 27B on lower side 27A on the left arm 28A, right arm 28B, or both arms 28A, 28B. FIG. 1G is a simplified front side view of area AA and FIG. 1H is a simplified back side view of area BB of the bony segment fixation system 10 shown in FIG. 1C with a retention module 20 removed according to various embodiments.

Figure 1H:
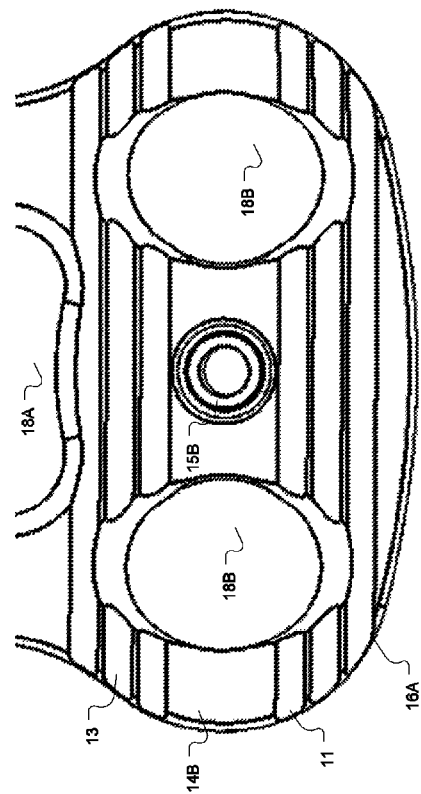
FIG. 1H is a simplified back side view of area BB of the bony segment fixation system shown in FIG. 1D according to various embodiments.

As shown in FIGS. 1G and 1H, the planar fixation element 11 may include a fenestration 15A extending between its front side 14A and back side 14B and complementary, female or reliefs 15C for the retention module's 20 detents or protrusions 27B. The retention module's 20 detents or protrusions 27B may be sized to releasably engage the reliefs 15C and engage the fenestration's 18B walls once rotated from a vertical orientation to a horizontal orientation as shown in FIG. 8F. The planar fixation element 11 fenestration's 15A minimum diameter may be greater than the retention module's 20 cylindrical extension's 26 maximum diameter, enabling the retention module 20 to rotate about the planar fixation element 11. The base of the retention module's 20 cylindrical extension 26 may be rotatably coupled to the planar fixation element's 11 back side via ring 15B in an embodiment.

Figure 5:
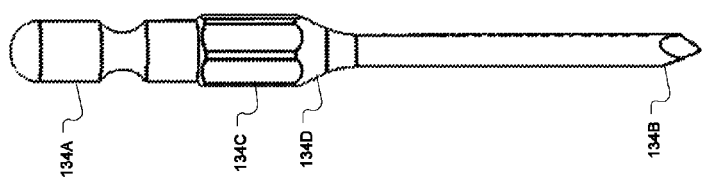
FIG. 5 is a simplified, side view of a fixation pin according to various embodiments.

As shown in FIGS. 1A-2D, the retention module 20 includes a fenestration 22 that is central to its arms 28A, 28B. The retention module's central fenestration's 22 minimum diameter may be greater than the maximum diameter of sections of temporary constructs 122, 132 that a practitioner may want to employ while implanting the bony segment fixation system 10 and bony fixation elements 142 to stabilize or couple two or more bony segments 222. In particular, the central fenestration's 22 minimum diameter may be greater than the maximum diameter of a distal section 124B of guide wire 122 (FIG. 3A) and a distal section 134B of a fixation pin 132 (FIG. 5).

During the implantation of a bony segment fixation system 10 with bony fixation elements 142, a practitioner may employ a guide wire 122 or fixation pin 132 to temporarily engage one or more bony segments 222. In particular, a practitioner may employ a temporary construct and visual or tactile verification of the constructs 122, 132 placement in a bony segment 222 prior to implantation of one or more larger diameter, permanent bony fixation elements (142), Such a process may prevent possible bony segment 222 wall extrusion by a bony fixation element 142, enable a practitioner to distract or compress bony segments 222 to increase or decrease the distance between bony segments 222, and ensure optimal placement of the bony segment fixation system 10.

Figure 8B:
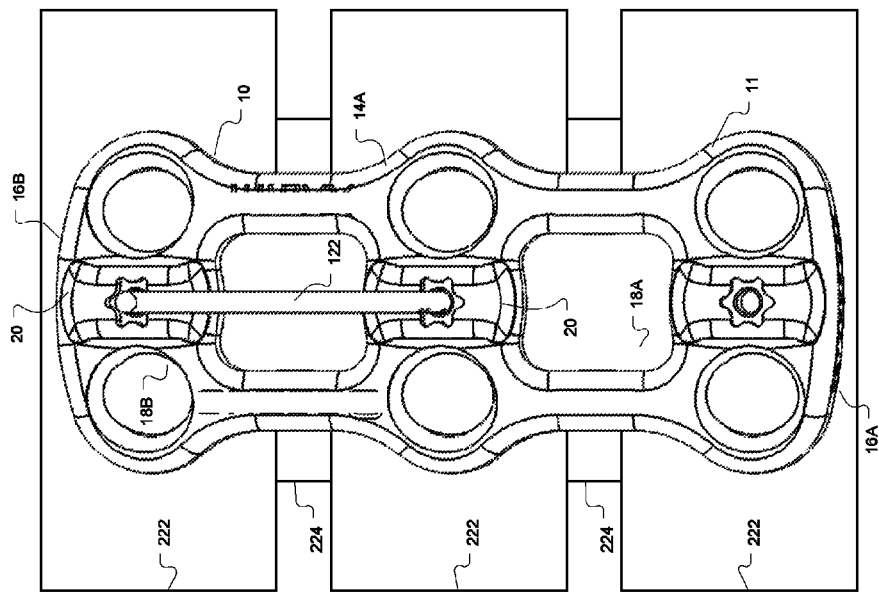
FIG. 8B is a simplified, front view of a bony segment fixation system operatively coupled to a first, center bony segment via a guide wire in its center retention module according to various embodiments.
Figure 8A:
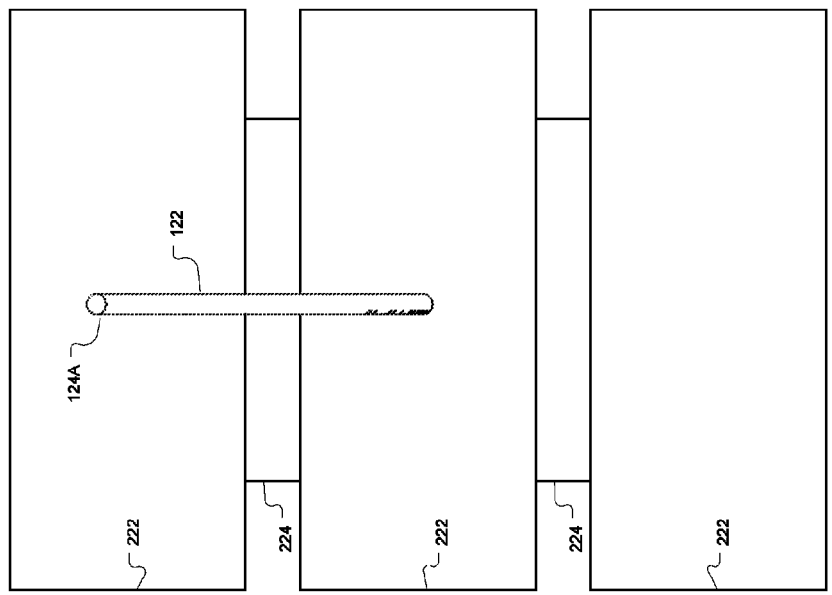
FIG. 8A is a simplified, front view of a guide wire coupled to a first, center bony segment according to various embodiments.

In an embodiment, the retention module 20 fenestration 22 is sized to enable a practitioner to move a segment of a temporary construct 122, 132 there-through. In addition in an embodiment, the center or axis of the fenestration 22 is approximately horizontally aligned with the one or more bony fixation element fenestrations 18B centers or axis for a bony segment 222 as shown by the dashed lines in FIG. 1B and FIG. 1C. Since the planar fixation element 11 is curved in an embodiment, the planar fixation element 11 must be rotated or tilted as shown in FIG. 1C to show the horizontal fenestration's center or axis alignment (18B and 22) for other retention modules 20 and bony fixation element fenestrations 18B. As shown in FIGS. 1A-1E, the planar fixation element 11 is configured to engage three bony segments 222. The planar fixation element 11 includes an upper section, middle section, and lower section to engage three different bony segments 222, each section including a retention module 20 and at least one bony fixation element fenestration 18B. It is not noted that the bony segments 222 may be all part of a single bone, such as a long bone with a facture to be fused, all separate bony segments 222 as shown in FIG. 8A, or other variations (two segments for one bony structure, and a third segment for another bony structure). As shown in FIG. 8A, the bony segments 222 are separate bony structures (vertebrae) separated by disc nucleus 224.

Figure 9:
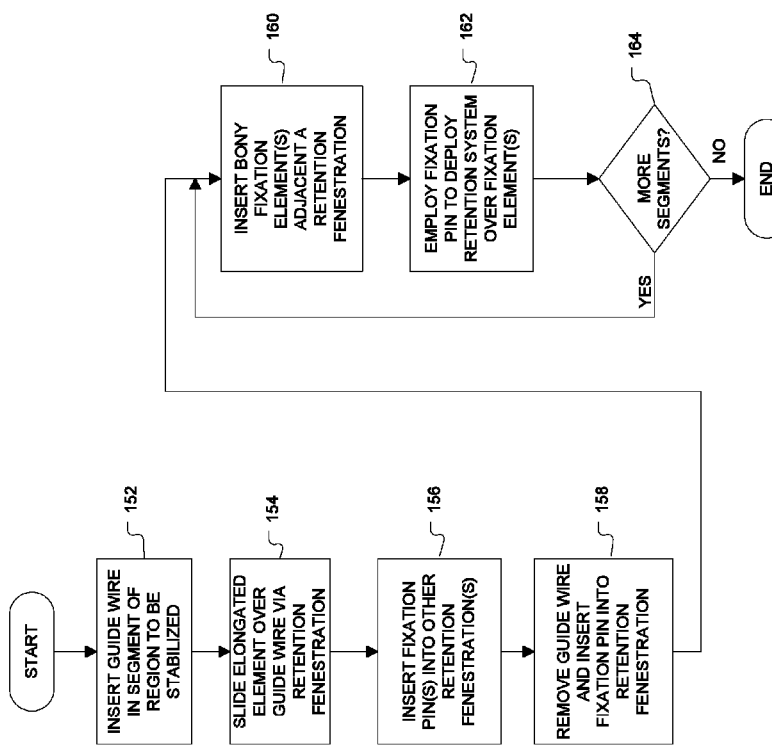
FIG. 9 is a flow diagram illustrating mammalian bony segment stabilization processing algorithms according to various embodiments.

In an embodiment, a practitioner may employ any, all, or any combination of the activities 152 to 164 of the algorithm 150 shown in FIG. 9 to couple a bony segment fixation system 10 according to an embodiment to two or more bony segments or sections 222. In an embodiment, a practitioner may first insert a guide wire 122 into one of several bony segments or sections 222 to be coupled to a bony segment fixation system 10 according to an embodiment (activity 152). FIG. 8A is a simplified, front view of a guide wire 122 coupled to a first, center bony segment according to various embodiments. As shown in FIG. 8A, an architecture 100 may include a guide wire 122 may be inserted into a location of a first bony segment or section 222 of three bony segments 222 separated by disc nucleus 224 where the bony segments 222 may be vertebrae in an embodiment. A practitioner may verify that the guide wire is placed in a desired location of the bony segment 222 via visual confirmation or tactile confirmation. A practitioner may employ an x-ray machine, Magnetic resonance imaging (MM) or other imaging system for visual confirmation of a guide wire 122, fixation pin 132, bony segment fixation system 10, and bony fixation elements 142.

Figure 3A:
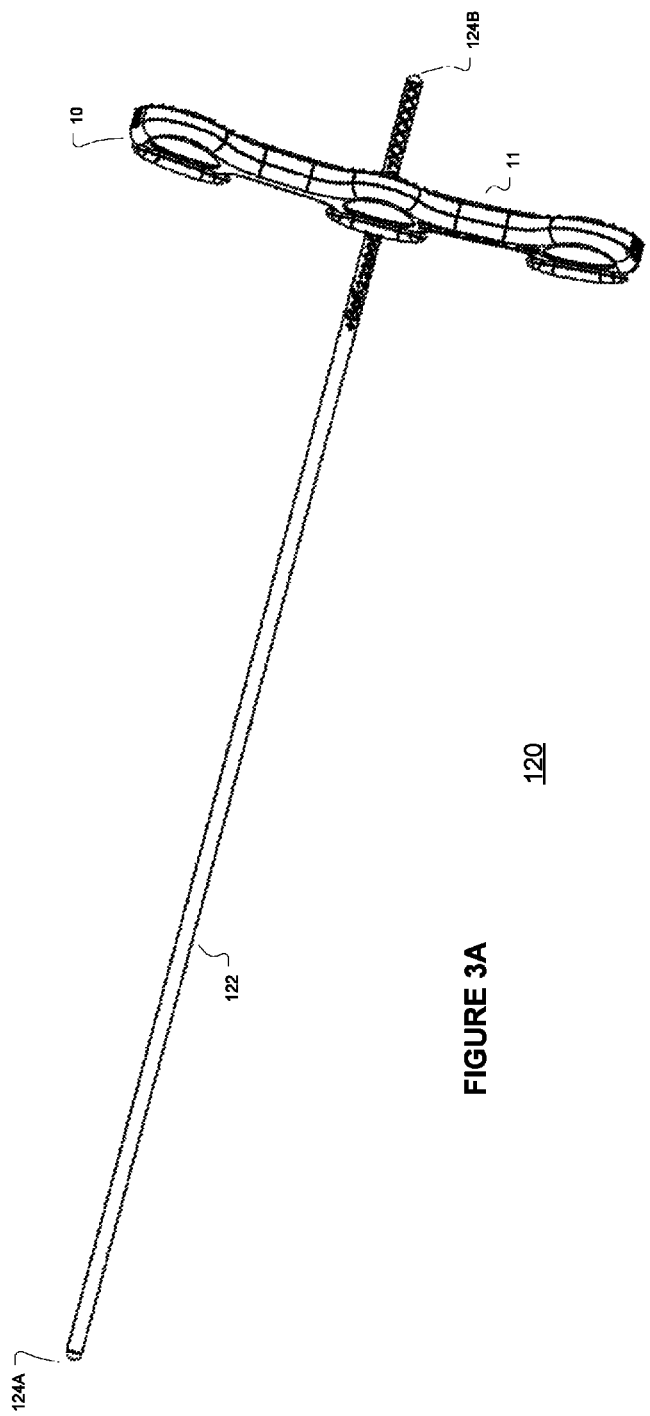
FIG. 3A is a simplified, isometric side view of a bony segment fixation system operatively coupled with a guide wire via a retention module according to various embodiments.
Figure 3B:
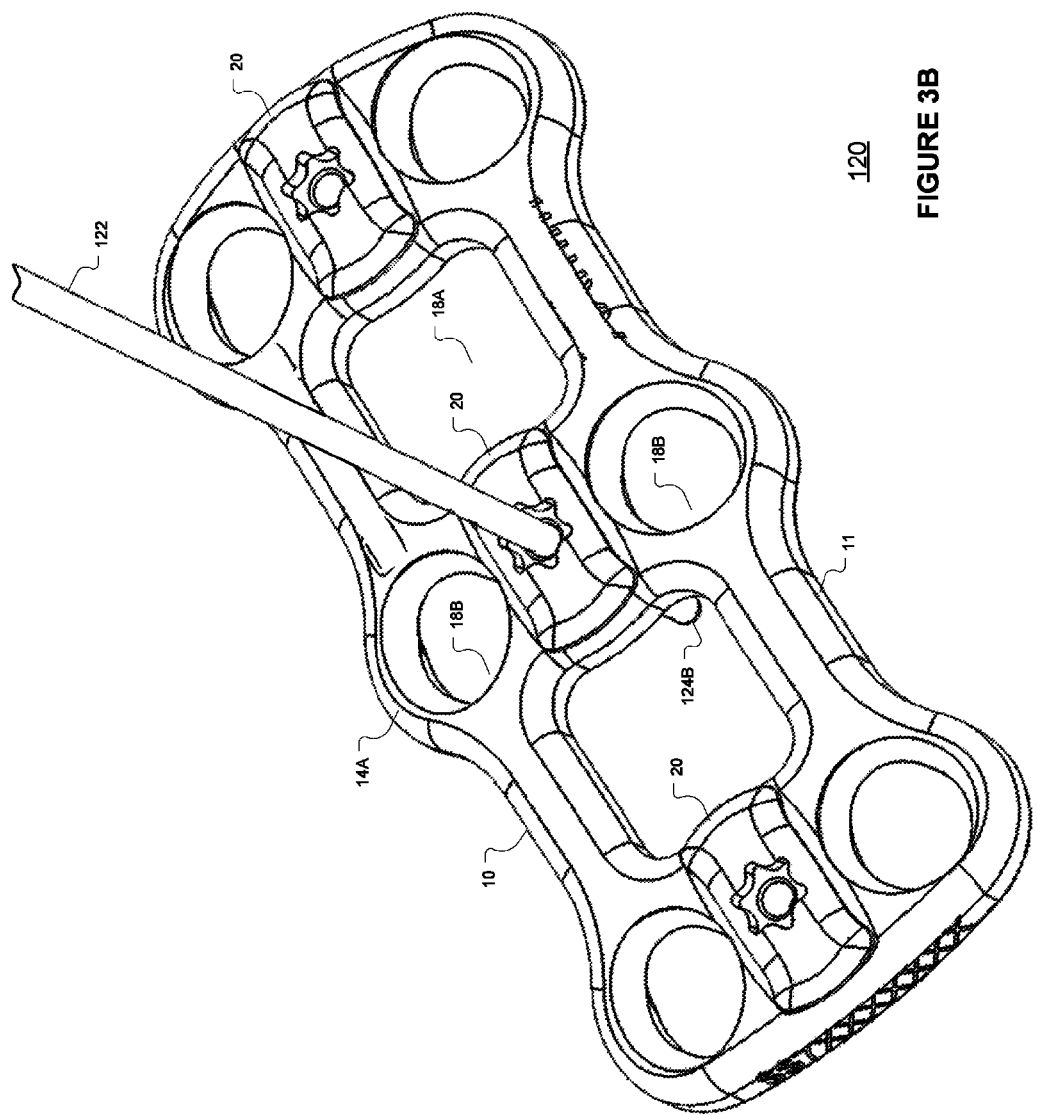
FIG. 3B is a simplified, partial isometric front view of a bony segment fixation system operatively coupled with a guide wire via a retention module according to various embodiments.

Once a practitioner verifies or confirms a guide wire 122 is properly placed in a bony segment 222, a practitioner may slide a bony segment fixation system 10 over the guide wire 122 proximal end 124A via one of the retention module 20 fenestrations 22 (activity 154). A practitioner may select the center retention module 20 fenestration 22 where they want to couple the bony segment fixation system 10 to a bony segment 222 above and below the bony segment 222 coupled to the guide wire 122 in an embodiment as shown in FIG. 8B. FIG. 3A is a simplified, isometric side view and FIG. 3B is a simplified, partial isometric front view of an architecture 120 including a bony segment fixation system 10 operatively coupled with a guide wire 122 via a retention module 20 according to various embodiments. As shown in FIGS. 3A and 3B the guide wire 122 may have distal section 124B and proximal end 124A.

Figure 8C:
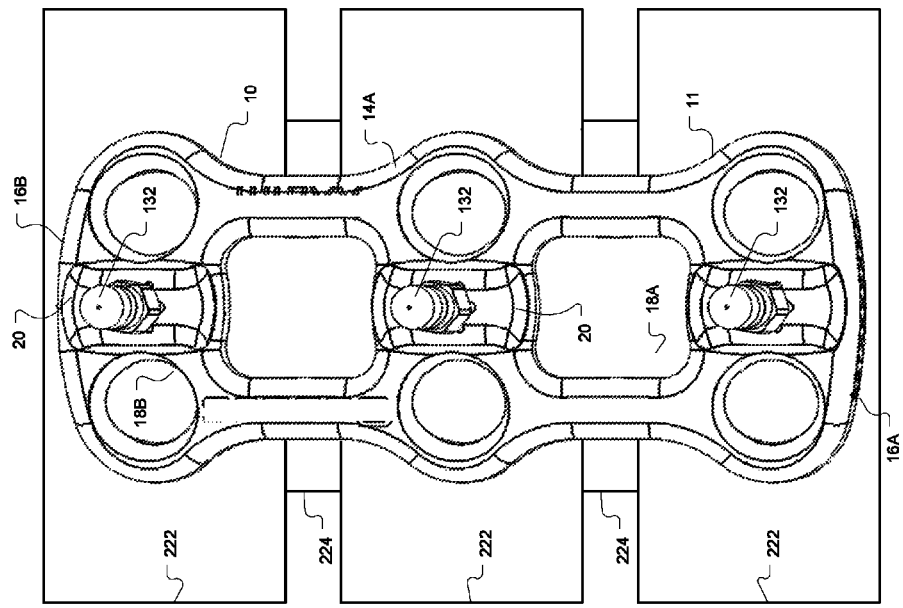
FIG. 8C is a simplified, front view of a bony segment fixation system operatively coupled to a first, center bony segment via a guide wire in its center retention module, operatively coupled to a second, upper bony segment via a first fixation pin in its upper retention module, and operatively coupled to a third, lower bony segment via a second fixation pin in its lower retention module according to various embodiments.

The guide wire 122 may have a maximum outer diameter that is less than the minimum diameter of the retention module 20 fenestration 22. In an embodiment, the guide wire 122 may have maximum diameter of about 1.5 mm to 3 mm. The guide wire may be formed of biocompatible materials including polymers and metals including stainless steel and nitinol. A practitioner may then insert a fixation pin (132, FIG. 5) into other bony segments 222 to be affixed or coupled to the bony segment fixation system 10 via one of the other retention module's 20 fenestrations in an embodiment (activity 156). FIG. 8C is a simplified, front view of a bony segment fixation system 10 operatively coupled to a first, center bony segment 222 via a guide wire 122 in its center retention module 20 fenestration 22, operatively coupled to a second, upper bony segment 222 via a first fixation pin 132 in its upper retention module 20 fenestration 22, and operatively coupled to a third, lower bony segment 222 via a second fixation pin 132 in its lower retention module 20 fenestration 22 according to various embodiments.

Figure 4B:
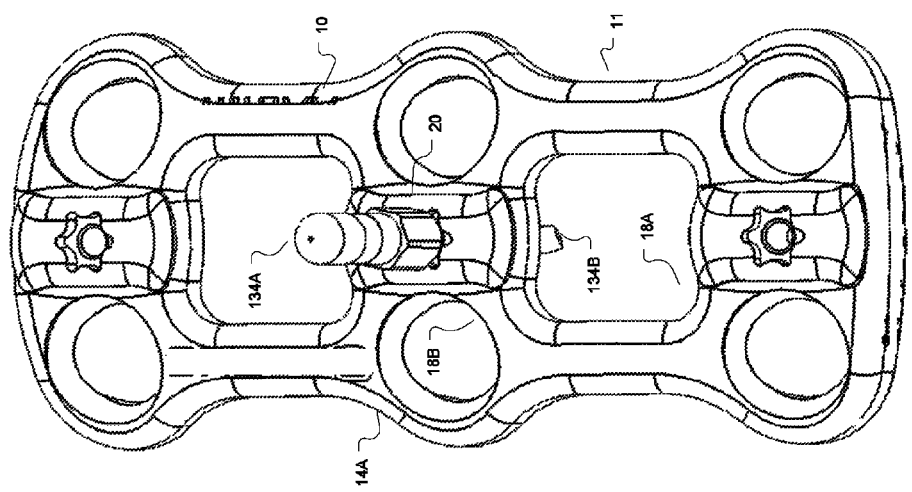
FIG. 4B is a simplified, front view of a bony segment fixation system operatively coupled with a fixation pin via a retention module according to various embodiments.

FIG. 4A is a simplified, isometric view and FIG. 4B is a simplified, front view of an architecture 130 including a bony segment fixation system 10 operatively coupled with a fixation pin 132 via a center (of three) retention module 20 fenestration 22 according to various embodiments. FIG. 5 is a simplified, side view of a fixation pin 132 according to various embodiments. As shown in FIGS. 4A, 4B, and 5, the fixation pin 132 may include a proximal end tool interface 134A, a second, retention module 20 tool coupling interface 134C, and a shaft reduction region 134D. In an embodiment, the distal section 134B may have a maximum diameter smaller than the minimum diameter of each retention module's 20 fenestration 22 while the shaft reduction region 134D may have a section (more proximal) with a maximum diameter greater than the minimum diameter of each retention module's 20 fenestration 22.

Accordingly, the fixation pin's 132 distal section 134B may be able to pass through a retention module's 20 fenestration 22 while the shaft reduction region is sized to limit its passage and enable its retention module 20 tool coupling interface 134C to operatively engage a retention module's 20 tool interface 24. In an embodiment, the fixation pin's proximally offset tool interface may include one or more protrusions (six in an embodiment) configured to operatively engaged mating recesses of a retention module's 20 tool interface 24. In such an embodiment, a practitioner may be able to use the fixation pin to both temporary couple the bony segment fixation system 10 to a bony segment 222 and rotate a retention module 20 to different positions via the retention module's 20 tool interface 24. The fixation pin's 132 proximal end tool interface 134A may be coupled to various tools via different connection interfaces including a Hudson interface and others. The tools may include various handles that enable a practitioner to insert the fixation pin 132 into a bony segment 222 via a retention module's 20 fenestration and rotate the retention module 20 about the fixation system's 10 planar fixation element 11.

Figure 8D:
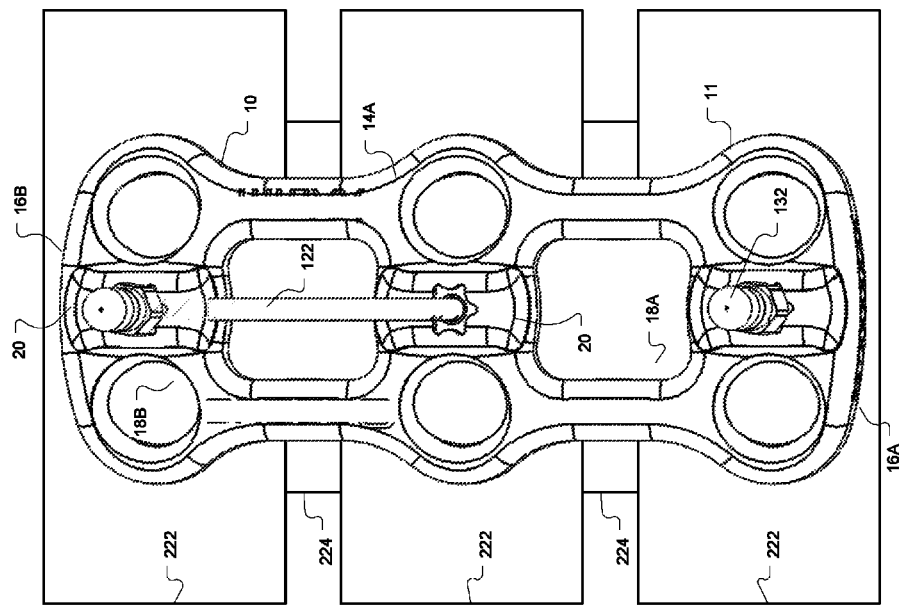
FIG. 8D is a simplified, front view of a bony segment fixation system operatively coupled to a first, center bony segment via a third fixation pin in its center retention module, operatively coupled to a second, upper bony segment via a first fixation pin in its upper retention module, and operatively coupled to a third, lower bony segment via a second fixation pin in its lower retention module according to various embodiments.

Once a practitioner has inserted fixation pins into one or more of other bony segments 222 via retention module's 20 fenestrations 22, the guide wire 122 may be removed and a fixation pin 132 may be inserted into the vacated retention module's 20 fenestrations 22 as shown in FIG. 8D (activity 158). The fixation pins 132 may temporarily couple the bony segment fixation system 10 to a plurality of bony segments 222. A practitioner may be able to verify that the fixation pins 132 are ideally placed into regions of bony segments 222 via fluoroscopy or other imaging techniques where the fixation pins 132 may be radio-opaque (absorb certain energy wavelengths). As noted in an embodiment, each fixation pin's 132 axis may be horizontally co-aligned with the fixation system's 10 plate's 11 bony fixation elements fenestrations center or axis 18B. Such a configuration may enable a practitioner to have horizontal placement confirmation of one or more bony fixation elements 142 in bony segment(s) 222 via fixation system's 10 plate's 11 bony fixation element fenestrations 18B as shown in FIG. 8E (activity 160).

Figure 6C:
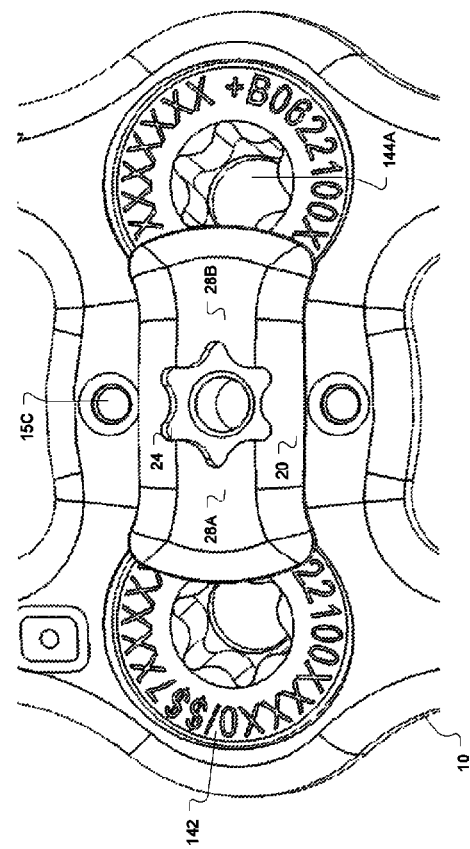
FIG. 6C is a simplified front side view of area CC of a bony segment fixation system operatively coupled with a bony segment fixation element as shown in FIG. 6B according to various embodiments.
Figure 6B:
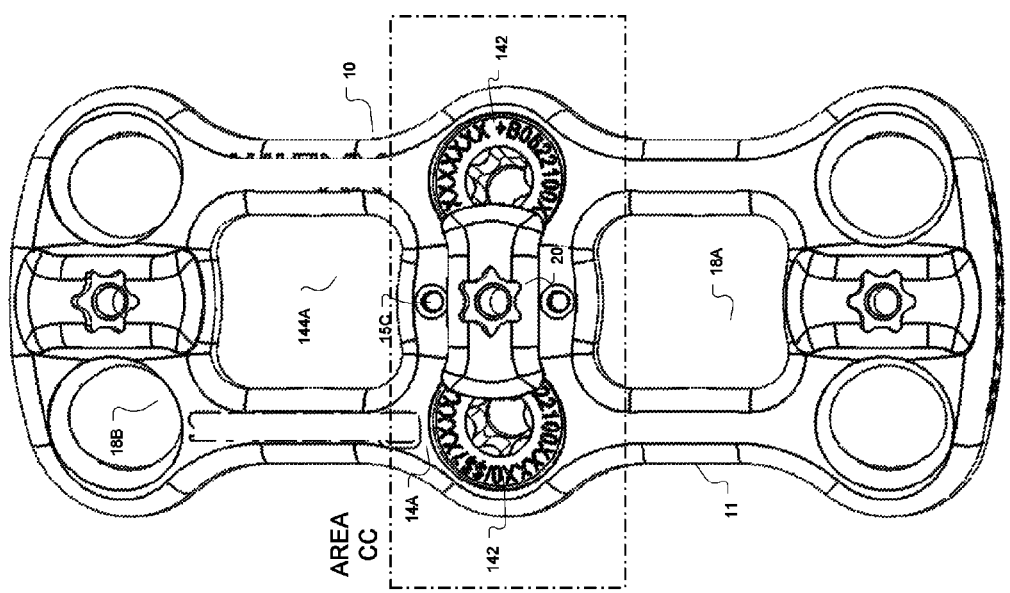
FIG. 6B is a simplified, front view of a bony segment fixation system operatively coupled with a bony segment fixation element according to various embodiments.

A practitioner may insert one or more bony fixation elements into bony segments 222 via a fixation system's 10 plate's 11 bony fixation element fenestrations 18B and then rotate a retention module 20 arms 28A, 28B from a first position (vertical) to a second position (horizontal) so one or more arms 28A, 28B are fixably aligned over a fixation system's 10 plate's 11 bony fixation element fenestrations 18B and seated bony fixation element's 142 head(s) 144E as shown in FIG. 8F (activity 162). FIG. 6A is a simplified, isometric view and FIG. 6B is a simplified, front view of architecture 140 including a bony segment fixation system 10 operatively coupled with several bony fixation elements 142 via a system's 10 fenestrations 18B according to various embodiments. FIG. 6C is a simplified front side view of area CC of architecture 140 including a bony segment fixation system 10 operatively coupled with several bony fixation elements 142 via a system's 10 fenestrations 18B as shown in FIG. 6B according to various embodiments.

As shown in FIGS. 6A-6C and 8F, the center retention module's 20 arms 28A, 28B may each extend over a bony fixation element fenestration 18B and implanted bony fixation element 142. In an embodiment, the retention module's 20 protrusions 27B may be sized to limit the unintentional rotation of retention module 20 arms 28A, 28B once moved over the fenestrations 18B and out of reliefs 15C (of planar fixation element 11). In an embodiment, the retention module's 20 protrusions 27B may also be sized to contact each bony fixation element's 142 head's 144E top surface. Such contact may limit undesired rotation of each respective bony fixation element 142. A practitioner may repeat the process of inserting bony fixation elements (activity 160) and deploying a corresponding retention module 20 arms 28A, 28B over the inserted or implanted bony fixation elements 142 (activity 162) for each bony segment 222 to be coupled to the bony segment fixation system 10 (activity 164).

It is noted that the bony segment fixation system 10 may be comprised of any biocompatible material including bone, polymers, and metals. Further a fixation system's 10 planar fixation element 11 may be formed of different materials than the retention module 20 in an embodiment.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus the following claims are hereby incorporated into the Detailed Description, with each claim standing on its own as a separate embodiment.

What is claimed is:

1. A bony segment fixation system for coupling a first bony segment to a second bony segment, the system including:
   a fixation plate having an elongated first axis and a second axis substantially orthogonal to the second axis, a front side, and a back side, the fixation plate including:
      a first bony fixation element fenestration extending from the plate front side to back side and located a first location along the plate's elongated first axis, the first bony fixation element fenestration having a minimum diameter greater than a maximum diameter of a bony fixation element distal segment to be inserted there through to fixably engage a first bony segment;
      a first retention module fenestration extending from the plate front side to back side and having a minimum diameter, the first retention module fenestration located approximately adjacent to first bony fixation element fenestration along the plate's elongated first axis; and
   a retention module having an elongated first axis, a front side, and a back side, the retention module including:
      a cylindrical extension extending from the retention module's back side for a length and located a first location along the retention module's elongated first axis and having a maximum diameter at a distal end less than the first retention module fenestration minimum diameter;
      a first arm offset from the cylindrical extension along the retention module's elongated first axis;
      a temporary bony fixation element fenestration co-aligned with the cylindrical extension and extending from the retention module front side to back side and through the length of the cylindrical extension, the temporary bony fixation element fenestration having a minimum diameter greater than a maximum diameter of a temporary bony fixation element's distal segment to be inserted there through to temporary fixably engage a bony segment; and
      a tool interface coaligned with the cylindrical extension and the temporary bony fixation element fenestration and inset in the retention module's front side.

2. The bony segment fixation system for coupling a first bony segment to a second bony segment of claim 1, wherein the retention module is rotatably coupled to the fixation plate via the retention module cylindrical extension and fixation plate first retention module fenestration.

3. The bony segment fixation system for coupling a first bony segment to a second bony segment of claim 2, wherein the retention module first arm includes a protrusion on the retention module back side, the first arm having a length and the protrusion shaped to engage a bony fixation element head when the bony fixation element is inserted into the first bony fixation element fenestration and the retention module first arm is rotated to extend over the fixation plate first bony fixation element fenestration.

4. The bony segment fixation system for coupling a first bony segment to a second bony segment of claim 3, wherein the fixation plate front side includes a relief shaped to releasably engage the protrusion on the retention module back side of the first arm when the retention module is rotated to a first position.

5. The bony segment fixation system for coupling a first bony segment to a second bony segment of claim 1, wherein the first retention module fenestration center is substantially vertically aligned with the first bony fixation element fenestration center.

6. The bony segment fixation system for coupling a first bony segment to a second bony segment of claim 1, the fixation plate further including a second bony fixation element fenestration extending from the plate front side to back side, the second bony fixation element fenestration having a minimum diameter greater than a maximum diameter of a bony fixation element distal segment to be inserted there through to fixably engage a first bony segment, the first bony fixation element fenestration located approximately adjacent to first retention module fenestration along the plate's elongated first axis on a first side, the second bony fixation element fenestration located approximately adjacent to first retention module fenestration along the plate's elongated first axis on a second, opposite side, wherein the first retention module fenestration is approximately centered between the first bony fixation element fenestration and the second bony fixation element fenestration along the plate's elongated first axis.

7. The bony segment fixation system for coupling a first bony segment to a second bony segment of claim 6, wherein the retention modules include a first arm offset from the cylindrical extension along the retention module's elongated first axis on a first side and a second arm offset from the cylindrical extension along the retention module's elongated first axis on a second, opposite side.

8. The bony segment fixation system for coupling a first bony segment to a second bony segment of claim 7, wherein the retention module is rotatably coupled to the fixation plate via the retention module cylindrical extension and fixation plate first retention module fenestration and the retention module first arm includes a protrusion on the retention module back side, the second arm includes a protrusion on the retention module back side, the first arm having a length and its protrusion shaped to engage a first bony fixation element head and the second arm having a length and its protrusion shaped to engage a second bony fixation element head when the first bony fixation element is inserted into the first bony fixation element fenestration, the second bony fixation element is inserted into the second bony fixation element fenestration, and the retention module is rotated so the first arm extends over the fixation plate first bony fixation element fenestration and the second arm extends over the fixation plate second bony fixation element fenestration.

9. The bony segment fixation system for coupling a first bony segment to a second bony segment of claim 8, wherein the fixation plate front side includes a first relief shaped to releasably engage the protrusion on the retention module back side of the first arm and a second relief shaped to releasably engage the protrusion on the retention module back side of the second arm when the retention module is rotated to a first position.

10. The bony segment fixation system for coupling a first bony segment to a second bony segment of claim 7, wherein the first bony fixation element fenestration center is substantially vertically aligned with the first retention module fenestration center on a first side and the second bony fixation element fenestration center is substantially vertically aligned with the first retention module fenestration center on a second side.

11. A bony segment fixation method for coupling a first bony segment to a second bony segment, the method including:
   placing a bony fixation system according to claim 3 over a first bony segment so the first bony fixation element fenestration and the temporary bony fixation element fenestration are positioned at desired sections of the bony segment; and
   placing a temporary bony fixation element's distal segment through the retention module's temporary bony fixation element fenestration to temporary fixably couple the bony segment fixation system to a first bony segment.

12. A bony segment fixation method for coupling a first bony segment to a second bony segment of claim 11, further including placing a bony fixation element's distal segment through the fixation plate's first bony fixation element fenestration to fixably couple the bony segment fixation system to a first bony segment.

13. A bony segment fixation method for coupling a first bony segment to a second bony segment of claim 12, wherein the bony fixation element is a bone screw and its distal segment includes a threaded shaft.

14. A bony segment fixation method for coupling a first bony segment to a second bony segment of claim 13, wherein the temporary bony fixation element is a bone pin having a long axis and includes a tool interface complementary to the retention module tool interface along its long axis.

15. A bony segment fixation method for coupling a first bony segment to a second bony segment of claim 13, wherein the first bony segment is a cervical vertebrae.

16. A bony segment fixation method for coupling a first bony segment to a second bony segment of claim 14, further including employing the temporary bone fixation element to engage the retention module's tool interface and rotate the retention module from the first position to the second position.

17. A bony segment fixation method for coupling a first bony segment to a second bony segment, the method including:
   placing a bony fixation system according to claim 7 over a first bony segment so the first bony fixation element fenestration, the second bony fixation element fenestration, and the temporary bony fixation element fenestration are positioned at desired sections of the bony segment; and
   placing a temporary bony fixation element's distal segment through the retention module's temporary bony fixation element fenestration to temporary fixably couple the bony segment fixation system to a first bony segment.

18. A bony segment fixation method for coupling a first bony segment to a second bony segment of claim 17, further including placing a first bony fixation element's distal segment through the fixation plate's first bony fixation element fenestration to fixably couple the bony segment fixation system to a first bony segment.

19. A bony segment fixation method for coupling a first bony segment to a second bony segment of claim 18, further including placing a second bony fixation element's distal segment through the fixation plate's second bony fixation element fenestration to further fixably couple the bony segment fixation system to a first bony segment.

20. A bony segment fixation method for coupling a first bony segment to a second bony segment of claim 19, wherein the temporary bony fixation element is a bone pin having a long axis and includes a tool interface complementary to the retention module tool interface along its long axis and the method further includes employing the temporary bone fixation element to engage the retention module's tool interface and rotate the retention module from the first position to the second position.

* * * * *